(12) United States Patent
Hossack et al.

(10) Patent No.: US 7,756,304 B2
(45) Date of Patent: Jul. 13, 2010

(54) MEDICAL DIAGNOSTIC ULTRASONIC IMAGING METHOD AND SYSTEM FOR DISPLAYING MULTI-PHASE, MULTI-FRAME IMAGES

(75) Inventors: John A. Hossack, Palo Alto, CA (US); Linyong Pang, Stanford, CA (US); Thilaka S. Sumanaweera, San Jose, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 09/369,510

(22) Filed: Aug. 6, 1999

(65) Prior Publication Data

US 2001/0012385 A1 Aug. 9, 2001

(51) Int. Cl.
*G06K 9/00* (2006.01)
(52) U.S. Cl. .................. 382/128; 128/922; 600/437
(58) Field of Classification Search ............... 128/660, 128/922; 600/433, 447, 440, 443, 437; 382/128; 364/518; 178/660
See application file for complete search history.

(56) References Cited

U.S. PATENT DOCUMENTS

| | | | | |
|---|---|---|---|---|
| 4,737,921 A * | 4/1988 | Goldwasser et al. | ......... | 364/518 |
| 5,488,952 A * | 2/1996 | Schoolman | .................. | 178/660 |
| 5,575,286 A | 11/1996 | Weng et al. | | |
| 5,582,173 A | 12/1996 | Li | | |
| 5,645,066 A * | 7/1997 | Gandini et al. | .............. | 128/660 |
| 5,655,535 A | 8/1997 | Friemel et al. | | |
| 5,782,766 A * | 7/1998 | Weng et al. | .................. | 600/443 |
| 5,817,022 A * | 10/1998 | Vesely | ......................... | 600/443 |
| 5,899,861 A | 5/1999 | Friemel et al. | | |
| 5,903,664 A | 5/1999 | Hartley et al. | | |
| 5,910,114 A | 6/1999 | Nock et al. | | |
| 5,913,823 A * | 6/1999 | Hedlberg | ...................... | 600/443 |
| 5,957,845 A * | 9/1999 | Holley et al. | ................. | 600/440 |
| 5,976,088 A * | 11/1999 | Urbano et al. | .............. | 600/433 |
| 5,993,390 A * | 11/1999 | Savord et al. | ............... | 600/437 |
| 6,004,270 A * | 12/1999 | Urbano et al. | .............. | 600/443 |
| 6,019,725 A * | 2/2000 | Vesely et al. | ................. | 600/447 |
| 6,110,117 A * | 8/2000 | Ji et al. | ........................ | 600/453 |
| 6,159,152 A * | 12/2000 | Sumanaweera et al. | ..... | 600/443 |

FOREIGN PATENT DOCUMENTS

| | | |
|---|---|---|
| DE | 197 46 936 A1 | 5/1998 |
| JP | 08-280688 | 10/1996 |
| JP | 09-327458 | 12/1997 |
| JP | 10-118061 | 5/1998 |
| WO | 97/32277 A1 | 9/1997 |

OTHER PUBLICATIONS

Japanese Patent Office Action (English translation) dated Jul. 14, 2008; 3 pgs.
Japanese Patent Office Action (English translation), Apr. 2009; 2 pgs.
Office Action dated Mar. 1, 2006 from German counterpart patent application No. 199 83 879.8-53, filed Jun. 28, 2001 (including translation); 5 pages total.

* cited by examiner

*Primary Examiner*—Vikkram Bali
*Assistant Examiner*—Katrina Fujita

(57) ABSTRACT

A medical diagnostic ultrasonic imaging system acquires image data for at least two frames at each of multiple positions, each frame identified with a respective phase of a physiological cycle. A multiphase 3-D or extended field of view data set is constructed from the image data. Then a plurality of images are generated from the multiphase data set. Each image is associated with a respective phase of the physiological cycle, and these images are displayed in sequence to a user.

7 Claims, 4 Drawing Sheets

MEDICAL DIAGNOSTIC ULTRASONIC IMAGING METHOD AND SYSTEM FOR DISPLAYING MULTI-PHASE, MULTI-FRAME IMAGES

BACKGROUND

This invention relates generally to medical diagnostic ultrasonic imaging techniques, and in particular to such imaging techniques that provide multiple images displayed in a sequence, wherein each image is associated with a respective phase of a physiological cycle.

U.S. patent application Ser. No. 08/916,585, filed Aug. 22, 1997, discloses a system for collecting single frames of image data from each of a plurality of spatial locations. Tracking information is collected with each frame, and this tracking information is used to assemble the frames into a static three-dimensional image or an extended field of view image. In three-dimensional imaging, the transducer probe is swept across a three-dimensional volume, and the tracking data is obtained along tracking planes oriented generally transverse to the image planes. In extended field of view imaging, the transducer probe is maintained within a plane such that multiple image frames are obtained in the same plane. The tracking information is then used to reconstruct an extended (typically elongated) field of view from multiple ones of the coplanar images. In both cases, the three-dimensional image or the extended field of view image is a static image. The entirety of the above-identified U.S. patent application Ser. No. 08/916,585 is hereby incorporated by its reference for its teaching of techniques for forming three-dimensional images and extended field of view images.

It is also known to acquire image frames from a particular part of the cardiac cycle. This can be done by triggering image acquisition at a specified time duration after a particular feature of the ECG signal, such as the R wave.

BRIEF SUMMARY

The present invention is defined by the following claims, and nothing in this section should be taken as a limitation on these claims.

By way of introduction, the preferred embodiments described below acquire image data for multiple frames at a plurality of transducer positions. Each frame is identified with a respective phase of a physiological cycle such as the heart cycle, and a multi-frame image data set is then formed from the acquired frames. This data set may be a multiphase three-dimensional data set or alternatively a multiphase extended field of view data set. Then multiple images are generated from the three-dimensional data set or the extended field of view data set, each image associated with a respective phase of the physiological cycle. These images are then displayed in sequence to a user. In this way the user obtains the advantage of multi-frame imaging (three-dimensional imaging or extended field of view imaging), along with the advantage of a display that sequentially shows the selected view for a sequence of phases of the physiological cycle.

DETAILED DESCRIPTION OF THE PRESENTLY PREFERRED EMBODIMENTS

Figure 1:
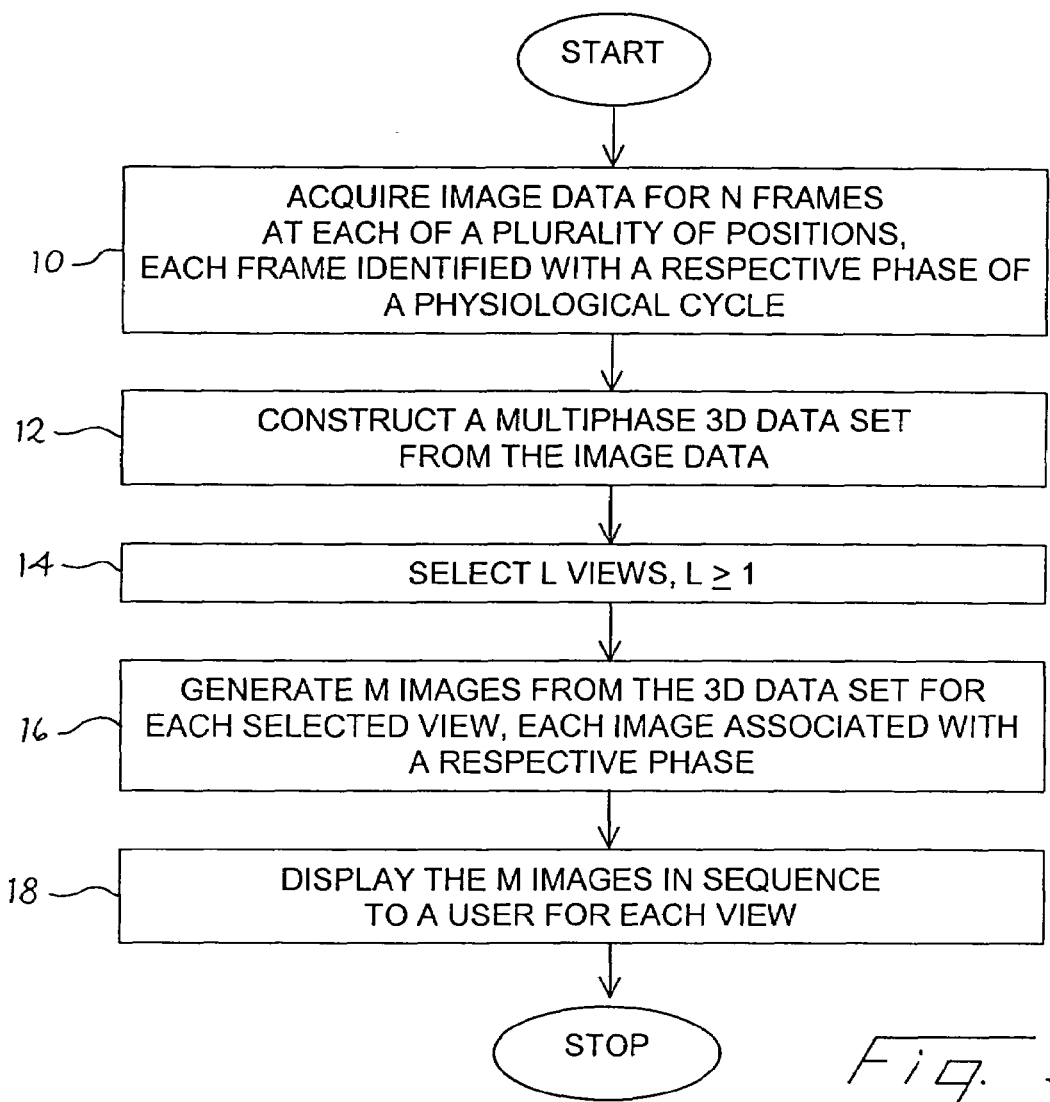
FIG. 1 is a flow chart of a method that incorporates a first preferred embodiment of this invention.

Turning now to the drawings, the method illustrated in FIG. 1 initially acquires image data for N frames at each of a plurality of transducer positions, wherein each frame is identified with a respective phase of a physiological cycle and N is greater than or equal to 2 (block 10). In one example, the image frames acquired in block 10 are each identified with a respective phase of an ECG signal. Typically, 10 to 25 frames of image data are acquired at each transducer position for each cardiac cycle. This represents a balance between computational requirements and adequate display of a moving image. For simplicity, the following example will consider the case where N equals 10, and 10 image data frames are collected for each transducer position. If the average ECG period is 1000 ms, this represents an interval of about 100 ms between consecutive frames of acquired image data. In general, it is preferable to acquire a large number of frames per heart cycle, but this will often lead to a large amount of data requiring a great deal of memory. The image data preferably comprises one or more of B-mode, color Doppler velocity, and color Doppler energy information.

In block 12 of the method of FIG. 1, the image data is used to construct a multiphase 3-D data set. That is, respective image data frames are associated with corresponding positions and phases with respect to a physiological cycle (e.g., the heart cycle as indicated by an ECG signal) in the 3-D data set.

Figure 2:
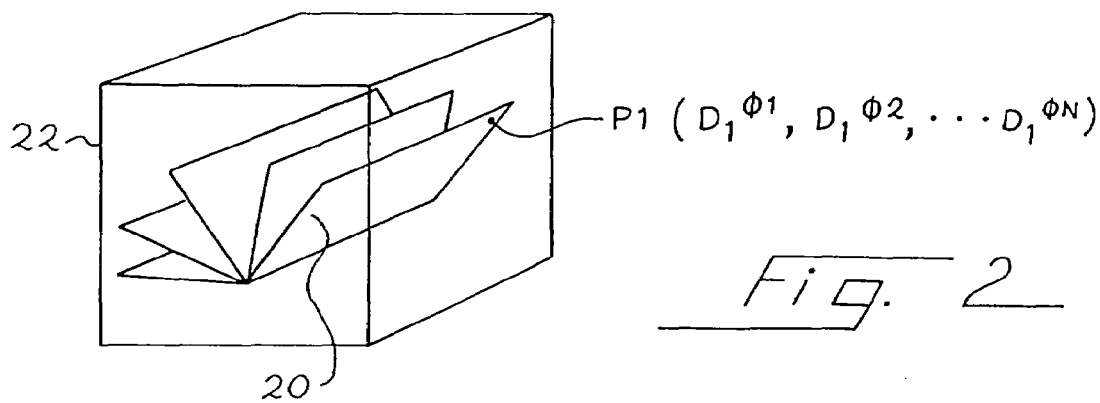
FIG. 2 is a schematic diagram illustrating a multiphase 3-D data set created using the method of FIG. 1.

FIG. 2 shows a schematic representation of the multiphase 3-D data set in which a plurality of frames 20 have been positioned within a three-dimensional volume 22. Each frame includes a plurality of data points, and the point P1 is indicated. P1 includes the data for point 1 for each of the N phases $\phi 1$ through $\phi N$, as schematically shown in FIG. 2.

In block 14 of FIG. 1, a series of L views is selected. L is an integer greater than zero, and the term "series" is intended broadly to cover one or more views. Typically, each view may be an arbitrarily positioned plane within a three-dimensional space. For example, each view may be slightly displaced from the previous view when L>1. Alternately, the selected view or views can be those appropriate for a surface rendering, a volume projection such as a maximum intensity projection, or multiple orthogonal slices.

In block 16, M images are generated from the 3-D data set for each of the selected views, each image associated with a respective phase with respect to a physiological signal. The same viewing calculation (e.g. extracting a two-dimensional view from the three-dimensional data set) is performed on the separate phases for each phase of the physiological cycle stored in the data set (10 in this example). This is repeated for all of the views.

In block 18, the M images for a given view are displayed in sequence to a user. This can be done by playing the M images sequentially on a video display at a frame rate equivalent to the acquisition rate. For example, if the phases are acquired at 100 ms intervals, then the output can be displayed at 100 ms intervals between consecutive frames. Preferably, the user is provided with means (not shown) for directing the system to play the images back at a faster or slower rate if desired, or to pick out static frames from the sequence. Alternately, the user of the system can change the view while cycling through the M cardiac phases. The user will perceive a pulsating object while the view is changing.

Figure 3:
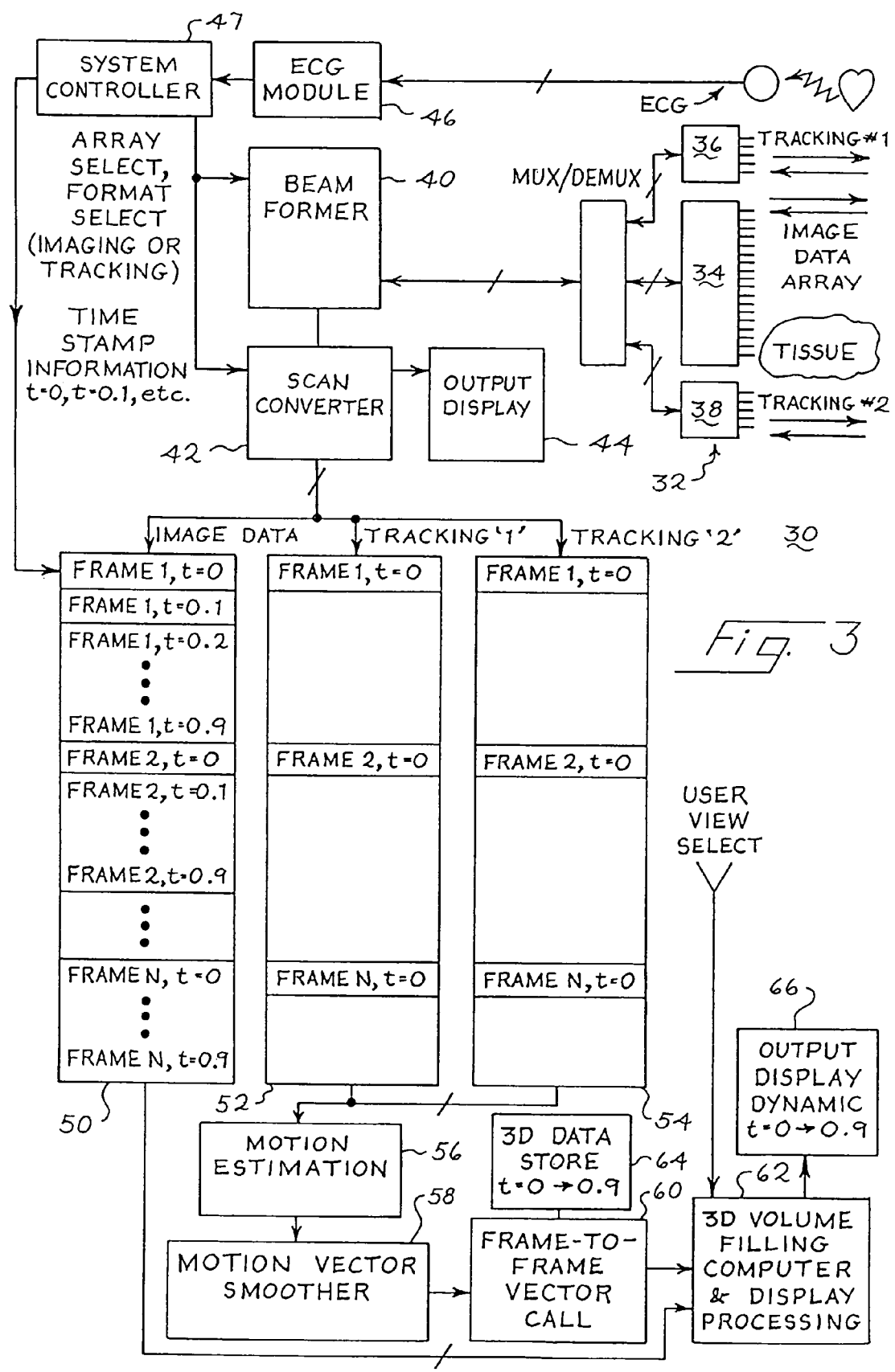
FIGS. 3 and 4 are schematic diagrams of alternative embodiments for practicing the method of FIG. 1.

FIG. 3 shows a block diagram of a medical diagnostic imaging system suitable for implementing the method of FIG. 1. The system illustrated in FIG. 3 is closely related to that disclosed in the above-identified U.S. patent application Ser. No. 08/916,585, and that application should be consulted for further details of operation.

Briefly, the system 30 includes a transducer probe 32 having an image transducer array 34 and first and second tracking transducer arrays 36, 38. Preferably, the tracking transducer arrays 36, 38 are oriented at right angles to the image transducer array 34.

The transducer probe 32 is connected to a transmit/receive beamformer 40 which is in turn coupled to a scan converter 42 and an output display 44. An ECG module 46 provides a signal indicative of the ECG cycle to a system controller 48.

The system controller 48 controls the beamformer 40 and the scan converter 42 to generate image data that is stored in a memory 50 and tracking data that is stored in memories 52 and 54.

In this example 10 frames of image data are stored in the memory 50 for each spatial position of the transducer probe, and each frame is time stamped with the respective phase with respect to the heart cycle. Tracking data is stored in memories 52 and 54 only for the first frame of each set of frames associated with a single position. Typically, the first frame in each set (t=0 in FIG. 3) is phased to a stable portion of the heart cycle, such as 30 milliseconds after the R wave. Of course, instead of the first frame after the R wave, position information may be stored for any desired phase of the heart cycle.

A motion estimator 56 estimates frame-to-frame motion, using the techniques described at length in U.S. patent application Ser. No. 08/916,585. In this case, one motion estimate determined from the selected phase is used for all phases of the cardiac cycle associated with the respective position. For example, all frames for position 1 are associated with the same estimate of motion that is determined for position 1 using the tracking data for t=0. This is believed to be a good approximation that saves a considerable amount of computational time. In some applications speckle may become decorrelated, and this may affect motion estimation accuracy. Therefore, in an alternate preferred embodiment, all frames are used to estimate motion. Motion estimates obtained by the motion estimator 56 are provided to a motion vector smoother 58, and the smoothed motion vectors are used to determine frame-to-frame vector motion in block 60. Computer 62 uses these frame-to-frame motion vectors to register the image data from the memory 50, as shown by way of example in FIG. 2. That is, the position information obtained from the block 60 is used to register the image data from the memory 50 by means of standard three-dimensional image interpolation. In this way the desired multiphase three-dimensional data set is constructed from the image data and is stored in the memory 64.

The user selects one or more views, and the computer 62 performs the necessary display processing to generate a plurality of images from the 3-D data set for each selected view, each image associated with the respective phase of the physiological cycle. These images are then displayed in sequence to a user on a display 66.

Figure 4:
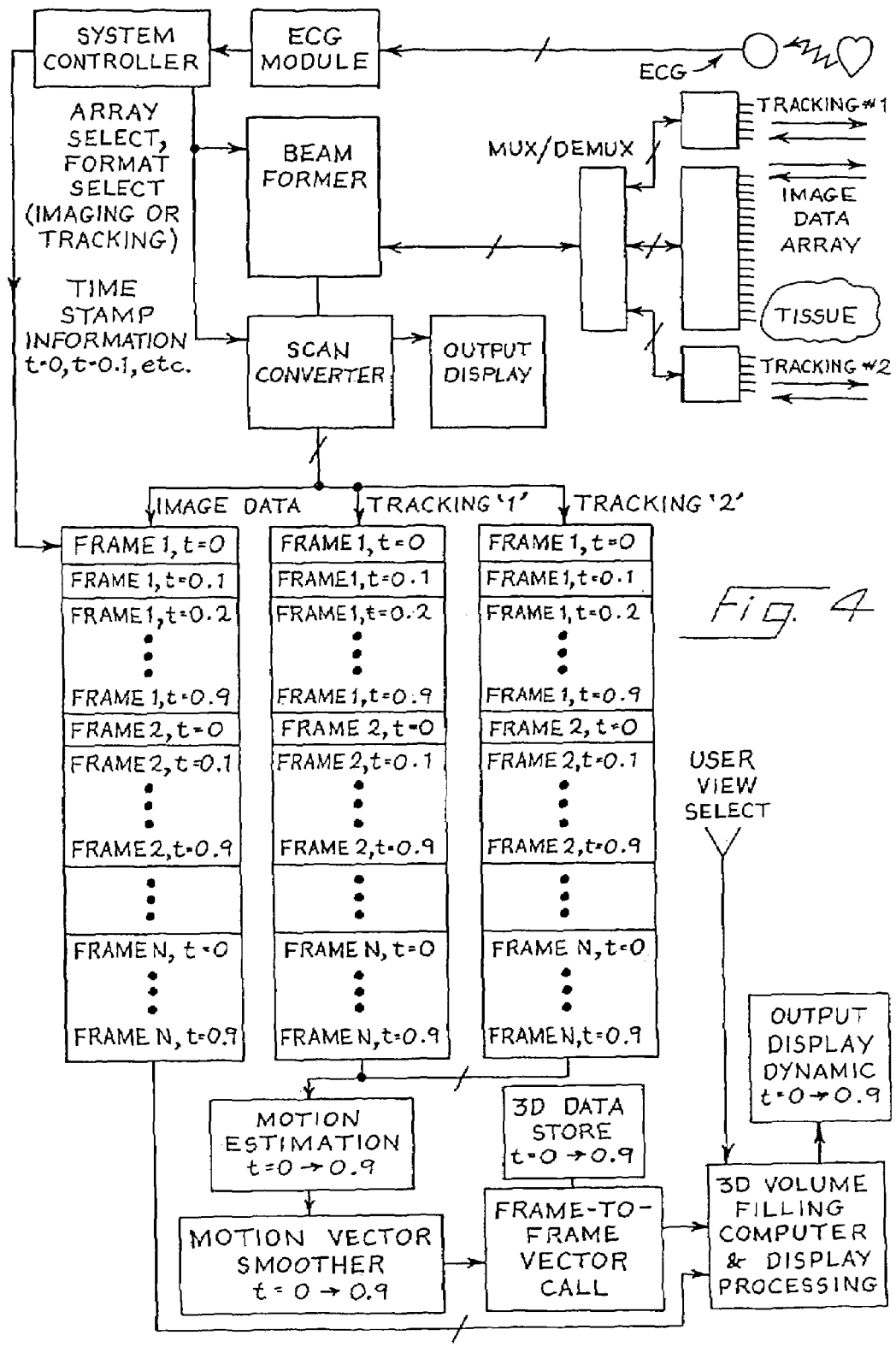

FIG. 4 shows an alternative, preferred embodiment that is similar to the embodiment of FIG. 3, except that the embodiment of FIG. 4 stores tracking data for frames of each phase. In this way tracking data is stored for all frames, not a subset of frames. The 3-D volume filling computer 62 creates a separate three-dimensional data set for each separate respective phase from the two-dimensional image frames associated with that phase, and the N separate 3-D data sets, taken together, can be considered a multi-phase 3-D data set. In other respects the embodiment of FIG. 4 operates similarly to that described above in conjunction with FIG. 3.

Figure 5:
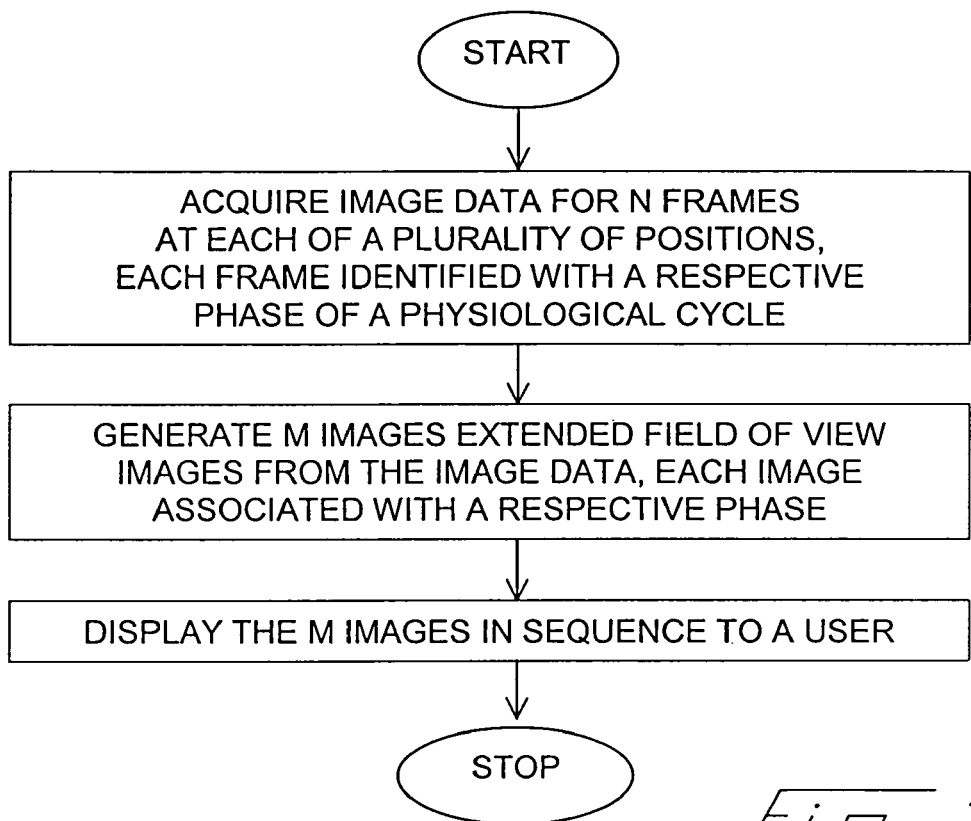
FIG. 5 is a flow chart of a method that incorporates a second preferred embodiment of this invention.

The foregoing discussion is related to three-dimensional data set embodiments of this invention. Other implementations of the invention relate to extended field of view imaging. As shown in FIG. 5, one preferred method acquires image data for N frames at each of a plurality of transducer positions, each frame identified with a respective phase of a physiological cycle. In this case the separate frames are coplanar. Next, M extended field of view images are generated from the image data, each image associated with a respective phase. Finally, the M images are presented in sequence to a user.

Figure 6:
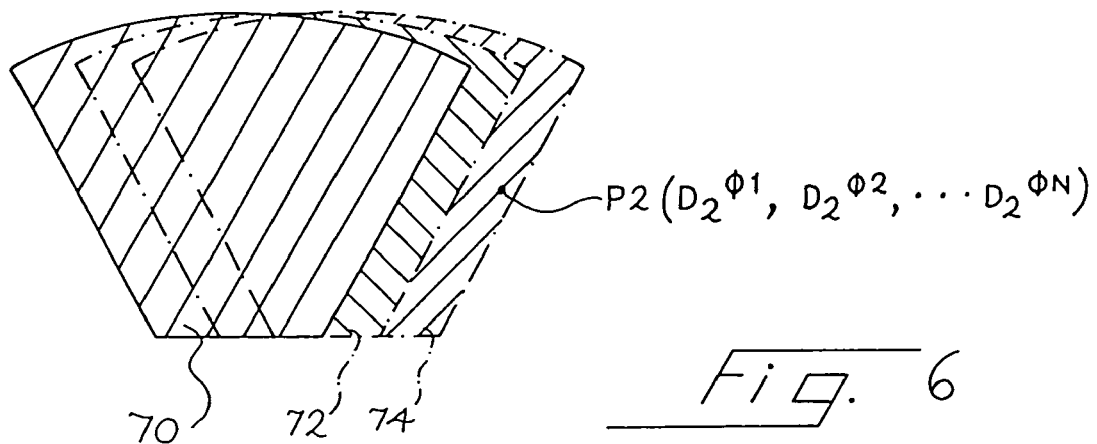
FIG. 6 is a schematic diagram of a multiphase extended field of view data set created using the method of FIG. 5.

FIG. 6 is a schematic diagram showing the manner in which three frames 70, 72, 74 are combined to produce an extended field of view. The cross-hatched fractions of the frame 72 and the frame 74 are combined with the cross-hatched portion of the frame 70 to produce an extended field of view that is elongated as compared to any one of the image frames. As shown in FIG. 6, the extended field of view data set is a multiphase data set in the sense that for each point, such as the point P2, image data is provided for each of N separate phases $\phi 1, \phi 2, \phi 3, \ldots \phi N$.

This alternative embodiment can be implemented in a manner similar to that described above in conjunction with FIGS. 3 and 4. In this case, the tracking data (which may be obtained from the image data) is preferably obtained in the same plane as the image data. The computer 62 forms the extended field of view data set including image information for each of the selected phases of the physiological cycle. The computer 62 then generates a sequence of extended field of view images from the image data, each extended field of view image associated with the respective phase of the physiological cycle.

Of course, many alternatives are possible to the preferred embodiments described above. For example, in some ultrasound systems an ECG signal is not available. One alternative for extracting a cardiac time reference is to detect the frame in which maximum Doppler flow velocity or energy is detected, for example by summing all energy levels for all color pixels and then dividing by the number of color pixels to derive mean energy. In this approach it is preferable to use a fast acquisition rate for detecting the maximum Doppler flow rate (such as 20 frames per second or higher). Regardless of the frame rate that is used for the purpose of detecting the Doppler flow maximum, only a subset of frames is preferably used for generating the multiphase 3-D data set or the multiphase extended field of view data set.

In the foregoing discussion, for both 3-D multiphasic imaging and for 2-D extended field of view multiphasic imaging, N frames are acquired for each of the plurality of transducer positions, each frame corresponding to a body cycle phase. In the more general case, the transducer can be continually moved while N frames are acquired. Furthermore, the number of frames acquired for successive body cycles may be different. Since the time stamp for the beginning of the body cycle (R-wave, for example) and the time stamps for each acquired images are known using the previously described means, M images, each associated with a respective phase of the body cycle, can still be generated.

Furthermore, this invention is not limited to use with cardiac cycles. Rather, it is well suited for use with a wide variety of physiological cycles, including the respiratory cycle.

As used herein, the term "multi-frame" as applied to a data set or an image means that data from two or more separate frames contribute to the data set or image. Though possible, it is not required that two or more entire frames contribute to the data set or image.

It should be apparent from the foregoing that a dynamic, multi-frame image display has been described which exhibits the advantages of three-dimensional imaging or extended field of view imaging in combination with the ability to acquire and present data from a sequence of phases of the selected physiological cycle.

The foregoing detailed description has described only a few of the many forms that this invention can take. For this reason this detailed description is intended by way of illustration and not by way of limitation. It is only the following claims, including all equivalents, that are intended to define the scope of this invention.

The invention claimed is:

1. An ultrasonic imaging method comprising:
   (a) acquiring image data for a plurality of frames, each frame identified with a respective phase of a physiological cycle;
   (b) generating a first extended field of view image from image data associated with a first phase of the physiological cycle from multiple selected ones of the frames of (a) associated with the first phase of the physiological cycle and acquired from substantially co-planar, partially-overlapping spatial regions;
   (c) generating a second extended field of view image associated with a second phase of the physiological cycle from image data from multiple selected ones of the frames of (a) associated with the second phase of the physiological cycle and acquired from substantially co-planar, partially-overlapping spatial regions; and
   (d) displaying at least the first and second extended field of view images in sequence to a user.

2. An ultrasonic imaging system comprising:
   (a) means for acquiring image data for a plurality of frames, each frame identified with a respective phase of a physiological cycle;
   (b) means for generating a first extended field of view image associated with a first phase of the physiological cycle from image data from multiple selected ones of the frames of (a) associated with the first phase of the physiological cycle and acquired from substantially co-planar, partially-overlapping spatial regions;
   (c) means for generating a second extended field of view image associated with a second phase of the physiological cycle from image data from multiple selected ones of the frames of (a) associated with the second phase of the physiological cycle and acquired from substantially co-planar, partially-overlapping spatial regions; and
   (d) means for displaying at least the first and second extended field of view images in sequence to a user.

3. An ultrasonic imaging method comprising:
   (a) acquiring image data for a plurality of frames;
   (b) extracting a time reference based on a Doppler characteristic of the image data of (a);
   (c) identifying each frame with a respective phase of a physiological cycle based at least in part on the time reference of (b);
   (d) generating a first image from image data associated with a first phase of the physiological cycle from multiple selected ones of the frames of (a) associated with the first phase of the physiological cycle;
   (e) generating a second image associated with a second phase of the physiological cycle from image data from multiple selected ones of the frames of (a) associated with the second phase of the physiological cycle; and
   (f) displaying at least the first and second images in sequence to a user.

4. The method of claim 3 wherein the Doppler characteristic of (b) comprises at least one of maximum Doppler flow velocity and maximum Doppler energy.

5. The method of claim 3 wherein (b) comprises:
   (b1) assessing mean Doppler energy for said plurality of frames.

6. The method of claim 5 wherein (b) further comprises:
   (b2) detecting one of the frames characterized by a maximum mean Doppler energy.

7. The method of claim 3 wherein the first and second images are respective extended field of view images created from selected frames of (a) acquired from substantially co-planar, partially overlapping spatial regions.

* * * * *